US010078060B2

(12) United States Patent
Geier et al.

(10) Patent No.: US 10,078,060 B2
(45) Date of Patent: Sep. 18, 2018

(54) HANDHELD INSTRUMENT AS WELL AS MOBILE DEVICE FOR X-RAY FLUORESCENCE ANALYSIS (71) Applicant: Helmut Fischer GmbH Institut fur Elektronik und Messtechnik, Sindelfingen (DE)

(72) Inventors: Udo Geier, Sindelfingen (DE); Bernhard Nensel, Karlsruhe (DE)

(73) Assignee: Helmut Fischer GmbH Institut für Elektronik und Messtechnik, Sindelfingen (DE)

( * ) Notice: Subject to any disclaimer, the term of this patent is extended or adjusted under 35 U.S.C. 154(b) by 97 days.

(21) Appl. No.: 14/805,926

(22) Filed: Jul. 22, 2015

(65) Prior Publication Data
US 2016/0033429 A1 Feb. 4, 2016

(30) Foreign Application Priority Data

Aug. 1, 2014 (DE) .......................... 10 2014 110 991
Oct. 22, 2014 (DE) .......................... 10 2014 115 383

(51) Int. Cl.
*G01N 23/223* (2006.01)
*G01T 7/00* (2006.01)

(52) U.S. Cl.
CPC ............ *G01N 23/223* (2013.01); *G01T 7/00* (2013.01); *G01N 2223/301* (2013.01)

(58) Field of Classification Search
CPC ........................... G01N 2223/301; G01T 7/00
See application file for complete search history.

(56) References Cited

U.S. PATENT DOCUMENTS 7,875,847 B2 * 1/2011 Dugas .............. G01N 35/00732
250/281
8,375,541 B1 * 2/2013 Beachy ................. B23B 47/281
29/26 A
(Continued)

FOREIGN PATENT DOCUMENTS

CN   2013 40400 Y   11/2009
CN   103364425 A    10/2013
(Continued)

OTHER PUBLICATIONS

European Search Report for corresponding European Patent Application No. 15 17 4787 dated Apr. 20, 2016.

*Primary Examiner* — David J Makiya
*Assistant Examiner* — Soorena Kefayati
(74) *Attorney, Agent, or Firm* — Renner, Otto, Boisselle & Sklar, LLP (57) ABSTRACT

A handheld instrument and a mobile device for x-ray fluorescence analysis has a housing and a handle, having an x-ray fluorescence measurement device by which a primary beam is directed onto a measurement surface of a measurement object through an outlet window, a detector which detects the secondary radiation emitted by the measurement surface, and a data processing device which controls a display. The outlet window on a front-side end of a first housing section and a positioning element is on the first housing section. A support element is on a further housing section, at a distance to the outlet window. The handheld instrument is aligned with respect to the measurement surface after the positioning on the measurement surface by the positioning element. The support element is positioned autonomously with respect to the measurement surface in a measurement position.

18 Claims, 10 Drawing Sheets

(56) References Cited

U.S. PATENT DOCUMENTS

| | | | |
|---|---|---|---|
| 8,745,889 B2* | 6/2014 | Fischer | G01B 7/105 33/572 |
| 9,335,280 B2* | 5/2016 | Pomerantz | G01N 23/223 |
| 2009/0057422 A1* | 3/2009 | Dugas | G01N 35/00732 235/494 |
| 2010/0226476 A1 | 9/2010 | Pesce et al. | |
| 2010/0278312 A1* | 11/2010 | Ortiz | G01N 23/223 378/195 |
| 2011/0079734 A1* | 4/2011 | Grodzins | G01N 21/63 250/461.1 |
| 2011/0142200 A1* | 6/2011 | Piorek | G01N 23/223 378/45 |
| 2013/0022166 A1* | 1/2013 | Drummy | G01N 23/223 378/44 |
| 2013/0114787 A1* | 5/2013 | Brown | G01N 23/04 378/57 |
| 2014/0098941 A1* | 4/2014 | Konkle | A61B 6/4283 378/189 |
| 2015/0041651 A1* | 2/2015 | Joung | G01T 7/00 250/336.1 |

FOREIGN PATENT DOCUMENTS

| | | | |
|---|---|---|---|
| EP | 2 549 266 A2 | 1/2013 | |
| EP | 2 896 959 A1 * | 7/2015 | G01N 23/04 |
| JP | 2012-229967 A | 11/2012 | |
| WO | 00/37928 | 6/2000 | |
| WO | 2008/100914 A2 | 8/2008 | |
| WO | 2013/052556 A2 | 4/2013 | |
| WO | 2013/112819 A1 | 8/2013 | |

* cited by examiner

HANDHELD INSTRUMENT AS WELL AS MOBILE DEVICE FOR X-RAY FLUORESCENCE ANALYSIS

This application claims priority of German Application No. 10 2014 110 991.0 filed Aug. 1, 2014, and German Application No. 10 2014 115 383.9 filed Oct. 22, 2014, which are hereby incorporated herein by reference.

The invention relates to a handheld instrument as well as a mobile device for x-ray fluorescence analysis.

In many fields of industrial production it is required to analyse coatings on objects and/or to detect the coating thickness thereof without contact. For this it is generally known to use an x-ray fluorescence method. Therein a primary beam is directed onto the measurement object from a radiation source. A secondary radiation emitted by the measurement surface of the measurement object is detected by a detector and transferred to an evaluation unit in order to determine, for example, the layer thickness and/or the element concentration thereof.

To implement an x-ray fluorescence method, until now so-called desktop instruments have been used which were set up permanently at a determined location due to their size and weight.

Furthermore, a handheld instrument having an x-ray measurement device for the implementation of the x-ray fluorescence analysis is known from US 2011/0142200 A1 which comprises a projection for the positioning of the handheld instrument on a measurement object close to an outlet window for the primary beam, said projection serving for the support on the measurement object and at the same time being formed as a collimator. Such a handheld instrument has the disadvantage that exact and defined positioning of the handheld instrument with respect to the measurement object is not thereby enabled.

The object of the invention is to propose a handheld instrument for the x-ray fluorescence analysis having an x-ray fluorescence measurement device as well as a mobile device for x-ray fluorescence analysis which is able to be transported as a unit, as well as a simple and secure handling both in the form of a desktop instrument and in the form of a handheld instrument.

This object is solved according to the invention by a handheld instrument for the x-ray fluorescence analysis consisting of a housing having a handle and an x-ray fluorescence measurement device arranged in the housing, in which the outlet window is provided on a front-side end of a first housing section of the housing and at least one positioning element is provided on the first housing section, allocated to this outlet window, and at least one support element is provided on at least one further housing section of the housing, at a distance to the outlet window, and the handheld instrument is aligned with respect to a measurement surface after setting on the measurement surface of the measurement object by the at least one positioning element and the at least one support element and independently assumes a measurement position with respect to the measurement surface and maintains the measurement position of the handheld instrument with respect to the measurement surface. Therefore a defined measurement position is assumed on the measurement object by the handheld measurement instrument without additional separate tools. At the same time, the handheld instrument independently assumes a stable position. Impairments during the measurement by changing the position and/or the angle of the measurement instrument with respect to the measurement surface are therefore eliminated. Additional adapters or attachments for the handheld instrument are therefore not required, as the handheld instrument stands independently on the measurement surface and remains aligned with respect to this after the setting of the handheld instrument on the measurement surface of the measurement object.

Preferably it is provided that a positioning element and two support elements or two positioning elements and one support element form a three-point support. Therefore a stable arrangement and support of the handheld instrument on the measurement object can occur. For example, the one positioning element can be formed as a surface which extends around the outlet window. The two support elements can then be formed in the form of a stand or as a prism or as two support points which are at a distance to each other, in particular semi-spherical or similar, and can be provided on the second housing section. The arrangement and design of the positioning elements and support elements for the formation of a three-point support can also be exchanged. Fundamentally, alternatively several positioning elements and/or support elements can also be provided for the formation of a self-retaining support for the handheld instrument.

Furthermore, it is preferably provided that the handle is provided on the first housing section and that the at least one further housing section is connected to the first housing section and/or to the handle. Therefore it can be enabled that the support elements are arranged on the further housing section and the second housing section is connected directly to the first housing section or to the handle in order to form a compact housing, in particular a self-contained housing.

Furthermore, preferably, a support element is formed as a support surface, adjacent to the outlet window or arranged thereon, and preferably the support elements arranged on the further housing section are formed as positioning feet or positioning prisms. This enables the x-ray fluorescence measurement device to only have to be calibrated once with regard to a measurement plane due to the defined support surface which preferably partially or completely surrounds the outlet window, as the measurement plane always lies in the support surface which surrounds the outlet window and the support surface is supported on the measurement surface. Furthermore, the advantage is provided that for smaller measurement objects, this can be supported in a simple way on the support surface for the implementation of the measurement. If, for larger measurement objects, an x-ray fluorescence analysis of the surface of the measurement object is implemented, the entire handheld instrument can be positioned thereon.

Preferably, the first housing section and the handle are formed to be pistol-shaped. The second housing section is arranged on the first housing section, in particular in the form of a magazine, such that a compact and manageable unit for such a handheld instrument is created. Preferably, the x-ray fluorescence measurement device is arranged at least partially in the second housing section. Preferably, furthermore, it is provided that the first housing section is formed to be tubular, bulbous, box-shaped or similar.

Furthermore, the outlet direction of the primary radiation is preferably aligned perpendicularly to the support surface. A detector of the x-ray fluorescence measurement device is positioned with respect to the outlet window in such a way that the emitted secondary radiation can be detected adjacent to the primary radiation which enters into the housing. Alternatively, the primary radiation can also exit from the outlet window at an acute angle to the support plane.

Furthermore, fastening elements are provided adjacent to the support elements or on the support elements themselves, said fastening elements serving to fix the handheld instrument to a receiver of the transport container or of a measurement table in the transport container. For example, a simple plug, clamp, screw connection can thereby be created. Additionally, the fastening elements and the support elements can interact together during fixing of the handheld instrument on the receiver in order to achieve a defined alignment of the handheld instrument with respect to the measurement table.

The handheld instrument preferably receives at least one accumulator in the handle. This is able to be exchanged and is preferably rechargeable.

A further preferred embodiment of the handheld instrument provides a display to output operational data on an end of the first housing section or of the housing which opposes the outlet window for the outlet of the x-ray radiation. The user can thereby follow individual pieces of measurement data or monitor settings directly during the implementation of a measurement.

Furthermore it is preferably provided that the data processing device arranged in the housing controls a radio interface for wireless communication with a data processing device which is provided separately to the handheld instrument, in particular a PC, a tablet, a smart phone or similar. A flexible and simple handling of the handheld instrument which is separate from a transport container or allocated to a measurement surface of the measurement object can thereby occur in order to control the handheld instrument and/or to take note of, evaluate or similar the detected measurement data.

Furthermore, it is preferably provided that the data processing device in the handheld instrument is able to be controlled by means of a remote control. The user can thereby control the handheld instrument for the implementation of a measurement, away from the measurement location. This can, for example, then be required if the handheld instrument must be set up in a sealed room and the user must be located outside of this room during the measurement. The same can apply for the measurement in a transport container without it therein being necessary that the handheld instrument is connected to the control and/or data processing device of the transport container via wire connections.

This object is furthermore solved by a mobile device which comprises a portable transport container, as well as a handheld instrument having an x-ray fluorescence measurement device provided thereon which is able to be arranged in the transport container and can also be completely removed from this transport container. A receiver is able to be arranged in the transport container which is also formed as a measurement table and can receive a measurement table, wherein the handheld instrument is able to be positioned in the transport container with respect to the measurement table. Such a mobile device has the advantage that the components required for the x-ray fluorescence analysis are able to be arranged and/or received together on and/or in the transport container and a simple handling is enabled during the transport and at the measurement location. Therefore, on the one hand it is enabled that the mobile device can be used in a conventionally known way as a desktop instrument at the measurement location, or if this is required, the handheld instrument can be removed completely from the transport container in order to position this directly on a measurement object such that a handheld measurement is also enabled on-site.

Furthermore, it is preferably provided that the transport container has a receiver on which the handheld instrument is able to be fastened releasably. Using such a receiver, on the one hand a secure transport of the handheld instrument in a defined stowage position in the transport container is enabled. Additionally, the handheld instrument can also assume a defined position with respect to the measurement table. Furthermore, the handheld instrument can also be removed simply in order to position this directly at a measurement location.

Furthermore, the handheld instrument can alternatively be able to be used in the transport container and the receiver for the handheld instrument can be able to be fixed in or on the transport container. Therefore a transport security of the handheld instrument in the transport container is enabled.

Preferably, this receiver of the transport container is formed on one side as a measurement table and receives the handheld instrument on the side which opposes the measurement table by means of a mount to which the handheld instrument is releasably fixed. Therefore this receiver can carry out a double function, whereby a reduction in construction space is enabled for the transport container.

This receiver preferably has a through-hole leading to the measurement table, through which the handheld instrument arranged on the opposing side can direct an x-ray fluorescence radiation onto a measurement surface of the measurement object which is supported on the measurement table. The handheld instrument is preferably also fastened in this through-hole. It is thereby enabled that the mobile device for x-ray fluorescence analysis is formed as a mobile desktop instrument in order to implement an x-ray fluorescence analysis in the case of a closed transport container.

The transport container preferably consists of a lower part and a cover which closes the lower part and which is arranged to be able to be folded back or to be able to be removed with respect to the lower part. An accessibility into the inner space of the transport container can be created through an opening of the cover, wherein in particular an accessibility to the measurement table for the introduction and removal of the measurement object is achieved, wherein the handheld instrument is positioned thereunder and in the inner space of the lower part. Therefore, after the positioning of the measurement object on the measurement table, the cover can be closed again and a shielded x-ray fluorescence analysis can be carried out in the closed transport container.

The receiver is advantageously able to be positioned on an upper edge of the lower part of the transport container or able to be arranged thereon. The handheld instrument can thereby be arranged in the inner space of the lower part during use of the mobile device as a desktop instrument and can be covered completely by the receiver such that only the measurement table is accessible from outside after opening the cover.

In a closed position of the cover, the receiver is advantageously fixed with respect to the inner space or lower part of the transport container. A secured stowage position of the receiver and/or of the handheld instrument is thereby enabled in the lower part in a simple manner in the case of a closed transport container.

A preferred embodiment of the mobile device provides that the receiver having a hinge joint is arranged on a side wall of the transport container, in particular on a valve, such that the receiver is able to be pivoted from a stowage position into a removal position for the handheld instrument. The stowage position would in this case be the arrangement of the receiver on the lower part such that the measurement table is accessible after opening the cover and the lower part having the handheld instrument located therein is closed by the support or the measurement table. This has the advantage that the receiver is arranged undetachably with respect to the transport container. Additionally, a good accessibility to the lower side of the receiver for the removal and the fastening of the handheld instrument can be enabled after the transfer of the receiver from the stowage position into the removal position which is able to be pivoted for example around an angle of 90° with respect to an arrangement as a measurement table. The stowage position of the receiver can at the same time also be the arrangement of the receiver in a horizontal plane as a measurement table.

Preferably, the handheld instrument is fastened releasably on the mount by a plug, clamp, screw connection or a bayonet lock or a combination thereof. A secure and quick release and re-attachment onto the mount can thereby be enabled with simple and few movements.

For the exact positioning of the handheld instrument with respect to the through-hole, preferably at least one centring and/or fixing section is provided on the handheld instrument or the mount or on both. A defined positioning of the handheld instrument with respect to the measurement table is thereby ensured. Therein, the handheld instrument can firstly be centred via the centring and/or fixing section after insertion into the housing by the fastening elements themselves which are arranged on the handheld instrument and can then assume a self-retaining position. Preferably, a sliding connection is provided to assume a defined position of the handheld instrument with respect to the receiver. This can still additionally be overlapped by a latching, which is able to be released.

The transport container preferably has an absorption element in the cover which is provided above the through-hole of the receiver in the case of the position thereof in a stowage position in the case of a closed position of the cover with respect to the lower part. It is thereby ensured that a proper shielding of the inner space of the transport container is provided in the case of an unintentional measurement by means of x-ray fluorescence without positioning a measurement object with respect to the through-hole.

The lower part of the transport container preferably has a display or a data processing device having a display which is able to be arranged to be able to pivot or to be removed on an outer side and which is able to be transferred from a non-use position to transport the transport container into a use position for the use of the device for x-ray fluorescence analysis. In a non-use position, the display or the data processing device having a display is aligned towards the inner space of the transport container such that a housing outer side of the display or the data processing device forms an outer wall of the transport container. The display is thereby protected from damages. In a use position which is preferably assumed by a pivot movement of the display, the corresponding measurement parameters can be entered directly at the mobile device and subsequently the measurement results can be visualised. Alternatively it is provided that instead of a pivotable display or data processing device, a removable tablet or similar is provided such that this display or the data processing device can also be separated from the transport container. In particular, this is advantageous if the transport container is not used as a desktop instrument, but rather the handheld instrument is positioned separated from the transport container on a measurement object, wherein at least the display can likewise be guided to the measurement location.

The transport container is preferably formed as an instrument which has the properties of a full-protection instrument. Accordingly, the wall thicknesses and the wall material are formed such that the x-ray radiation cannot reach outside or only below a threshold value determined by x-ray regulations. Additionally, individual circuit breakers and/or sensors are provided in the housing such that an x-ray fluorescence measurement in the transport container can only then be implemented and triggered if, for example, the cover is closed. The closed position of the cover can, for example be detected via a sensor element in the lower part which is connected to a control device or data processing device.

In the case of the mobile device it is preferably provided that the handheld instrument and the data processing device communicate wirelessly with each other in the transport container. This can occur via a Bluetooth connection, a WLAN connection, an infrared interface or similar. Alternatively, it can also be provided, in particular in the case of a display which is arranged to be able to pivot or a data processing device which is arranged to be able to pivot on the lower part of the transport container, that a wired communication is provided. For example, a signal transfer line can also be able to be connected from the transport container to the handheld instrument or to the display or to the data processing device. The communication with regard to the data processing device, the display and the handheld instrument is also dependent on the construction. For example, it can be provided that the data processing device is installed in a fixed manner in the transport container such that a communication between a pivotable and/or removable display and the removable handheld instrument is enabled. If the display and the data processing device are composed in one instrument, such as, for example, in the case of a tablet, a direct communication with the handheld instrument can be enabled.

Furthermore it is preferably provided that the transport container has a central lock. Therefore both the outer housing part of the display or the data processing device and the cover can each be held in a secure closed position. For this, advantageously a latch mechanism is provided which at the same time engages with an upper side of the housing part of the display or the data processing device as well as a side wall of the cover which is arranged to be adjacent to this.

The invention as well as further advantageous embodiments and developments of the same are described and explained in more detail below by means of the examples depicted in the drawings. The features to be gleaned from the description and the drawings can be applied individually or together in any combination according to the invention. Here are shown.

Figure 1:
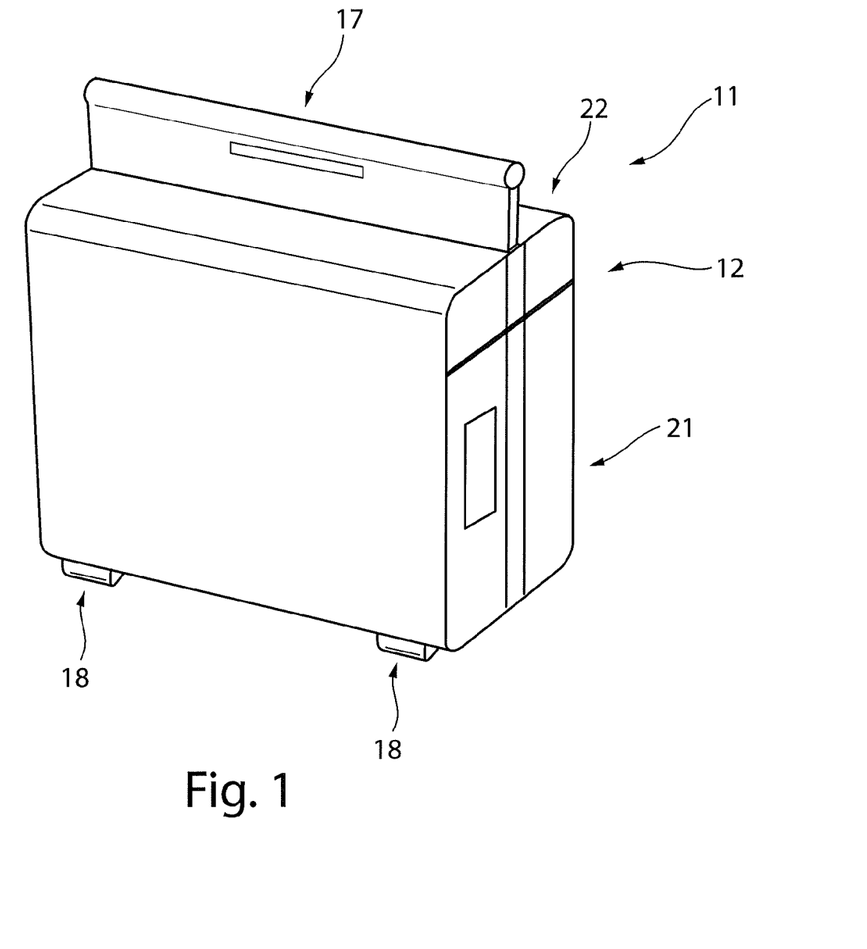
FIG. 1 a perspective view of a transport container of a mobile device for x-ray fluorescence analysis, FIG. 2 a perspective view of a handheld instrument having an x-ray fluorescence measurement device, FIG. 3 a perspective view of the mobile device in a use position as a desktop instrument, FIG. 4 a perspective view of the mobile device in a further use position during a measurement, FIG. 5 a perspective view of a further use position of the mobile device according to FIG. 1 to remove the handheld instrument, FIG. 6 a further schematic view of the use position of the mobile device according to FIG. 5 during the removal of the handheld instrument, FIG. 7 a schematic view in a further use position of the mobile device during the removal of the handheld instrument, FIG. 8 a schematic view from the front onto the use position according to FIG. 7, FIGS. 9a and 9ab schematic detailed views for fixing the handheld instrument on the mobile device, FIG. 10 a schematic side view in the partial section of the transport container in FIG. 1 and FIG. 11 a schematic view of the handheld instrument in use on a measurement surface of a measurement object.

In FIG. 1, a mobile device 11 for x-ray fluorescence analysis is depicted perspectively in a transport state. This mobile device 11 consists of a transport container 12 which is depicted in a closed position in FIG. 1 and a handheld instrument 14 which is depicted perspectively in FIG. 2. Furthermore, the mobile device 11 for x-ray fluorescence analysis comprises at least one data processing device which is not depicted in more detail, as well as a display 16 which is depicted, for example, in FIG. 3. This display 16 can also be part of a data processing device, such as, for example, a computer, a tablet or similar, which can also be removable from the transport container 12. Likewise, it can be provided that the data processing device is provided in the transport container 12 and only a display device, in particular a display, is able to be removed from the transport container 12, wherein the data transfer preferably occurs wirelessly.

The transport container 12 is formed to be cage or box-shaped having a handle 17. This transport container 12 comprises stands 18 for the stable and fixed support of the transport container 12 on a surface.

Figure 3:
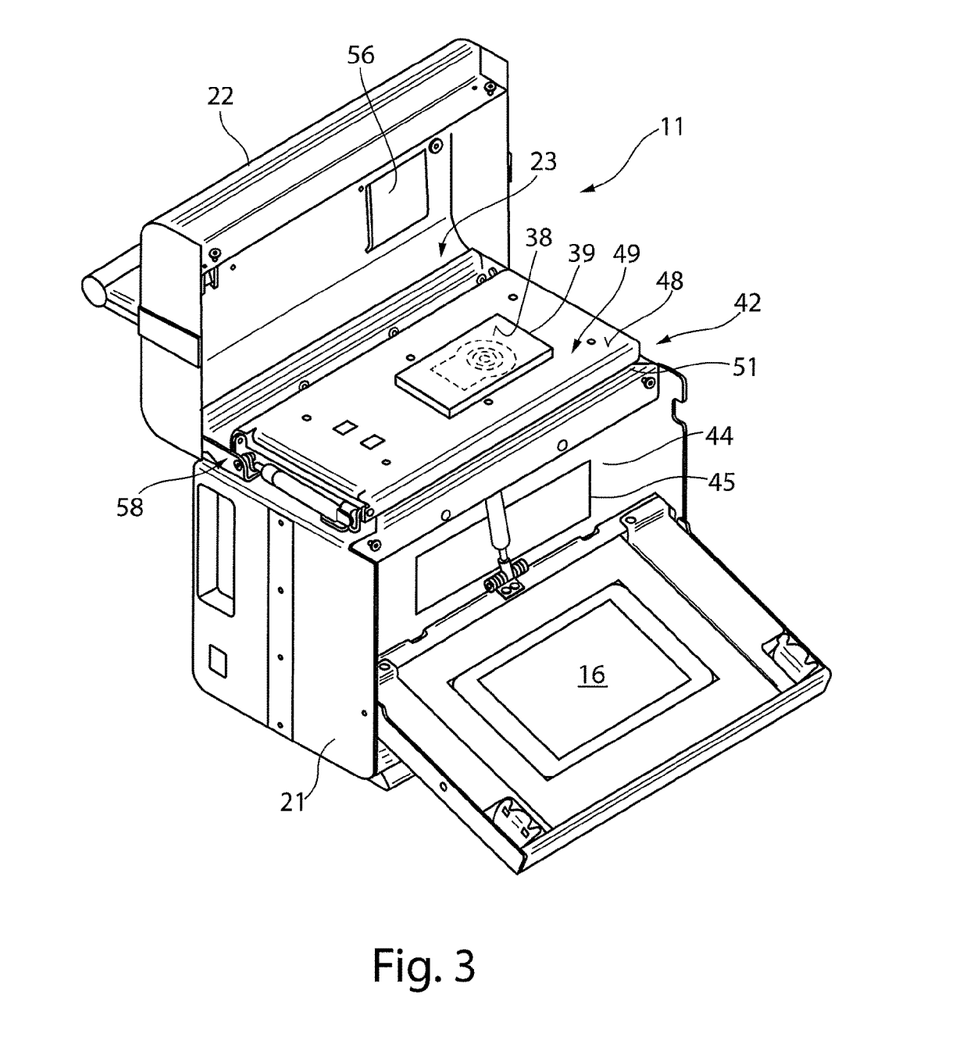

The transport container 12 comprises a lower part 21 as well as a cover 22 which is depicted in FIG. 1 in a closed position and in FIG. 3 in an open position. Preferably, the cover 22 is connected to the lower part 21 via a hinge 23 (FIG. 3). Alternatively, this can also be able to be completely removed.

Figure 2:
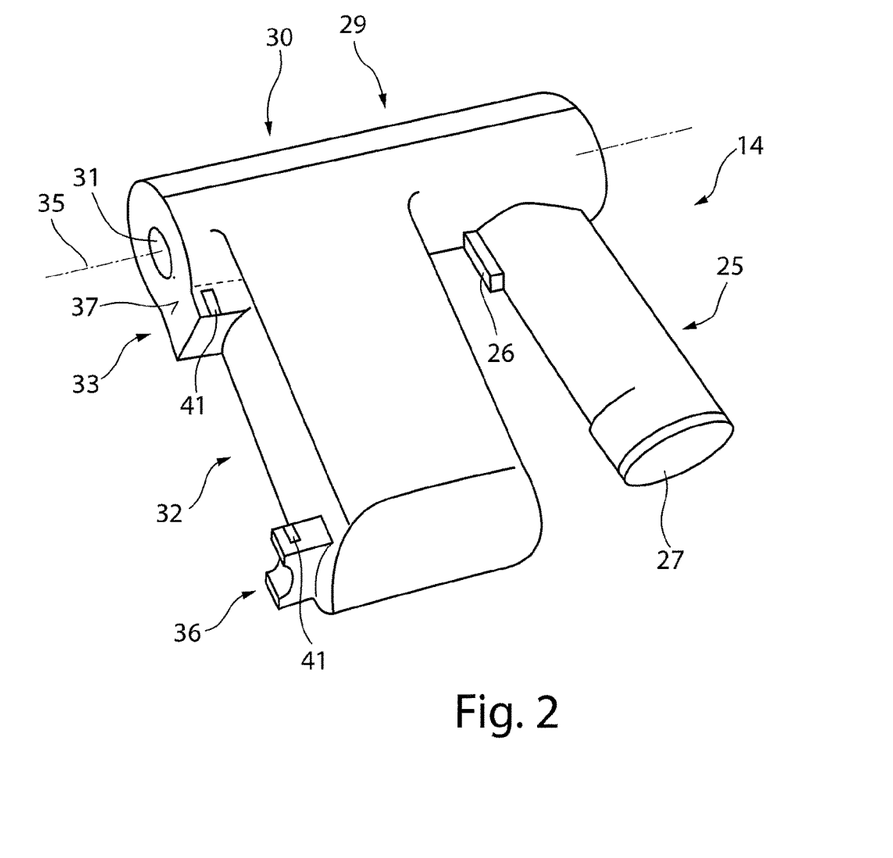

The handheld instrument 14 depicted in FIG. 2 is arranged in an inner space of the transport container 12 and can be removed from this completely. The handheld instrument 14 comprises a handle 25, for example having an operating button 26. In the handle 25, an accumulator 28 (FIG. 5) can be able to be inserted into the handle 25 via a removable lock 27. The handle 25 is connected to a first housing section 30 of the housing 28 which has an outlet window 31 on an end from which a primary radiation exits. A further housing section 32, in particular in the form of a magazine, is provided on the first housing section 30, adjacent to the outlet window 31. An x-ray fluorescence measurement device is provided in this housing section 32 as well as at least partially in the housing section 30, said x-ray fluorescence measurement device comprising a radiation source to emit the primary beam as well as a detector to detect a secondary radiation emitted by a measurement surface 38 and an evaluation device. A slide can be provided on an upper side of the first housing section 30, using which the outlet window 31 is able to be closed.

Figure 11:
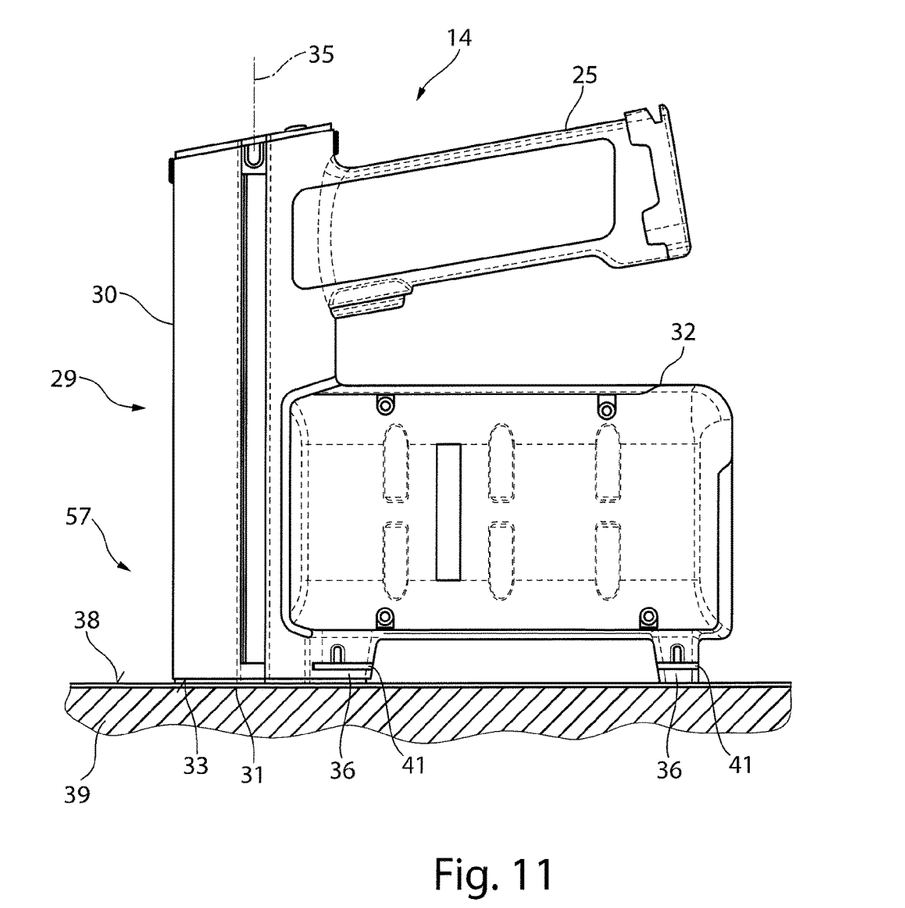

An outlet direction of the primary radiation advantageously lies in a longitudinal axis 35 of the first housing section 30. Positioning elements 33 are preferably provided on the first housing section 30 in a plane at right angles to this. Furthermore, at least one support element 36 is provided on the second housing section 32. The support surfaces or contact surfaces of the at least one positioning element 33 and of the at least one support element 36 can lie in a mutual plane in order to position the handheld instrument 14 on a measurement surface 38 of a measurement object 39 directly on site in the case of a mobile use, as this is depicted in FIG. 11. Preferably, the at least one positioning element 33 and the at least one support element 36 are formed as a three-point support. The positioning element 33 which is allocated to the outlet window 31 is, for example, formed by a support surface 37 which is flush to the outlet window 31. Alternatively, the outlet window 31 can also be offset backwards slightly with respect to the support surface 37 or the at least one positioning element 33 in the direction of the housing section 30, wherein preferably a predetermined spacing is specified such that the spacing of the measurement surface 38 and the x-ray fluorescence device, in particular a collimator and/or detector, is specified. The further support elements 36 which are arranged on the further housing section 32 are preferably formed as two positioning feet which preferably have a prismatic geometry lying therebetween such that a centring and/or positioning of the handheld instrument 14 can occur via this prismatic support of the support elements 36 arranged on the housing section 32 during the positioning of the handheld instrument 14 on a tube or a curved surface and the support surface 37 is only supported linearly at the highest point of the tubular or curved measurement surface. Alternatively, the at least one positioning element 33 can also have a support prism or spaced support points and the support element 36 can be provided as a dotted or planar as well as prismatic support.

The handheld instrument 14 can assume a position, as this is depicted in FIG. 11. The handheld instrument 14 is arranged to be self-retaining with respect to the measurement surface 38 and assumes its measurement position 57 autonomously. The support elements 36 are preferably at a distance to one another in order to ensure a predetermined alignment of the longitudinal axis 35 of the first housing section 30 via such a three-point support and therefore to ensure a primary radiation exiting from the outlet window 31. Fastening elements 41 are provided on the housing 29 or the housing sections 30, 32, adjacent to the at least one positioning element 33 and/or the at least one support element 36, the function of which fastening elements 41 shall be described in more detail below by means of FIGS. 5 to 7.

Figure 4:
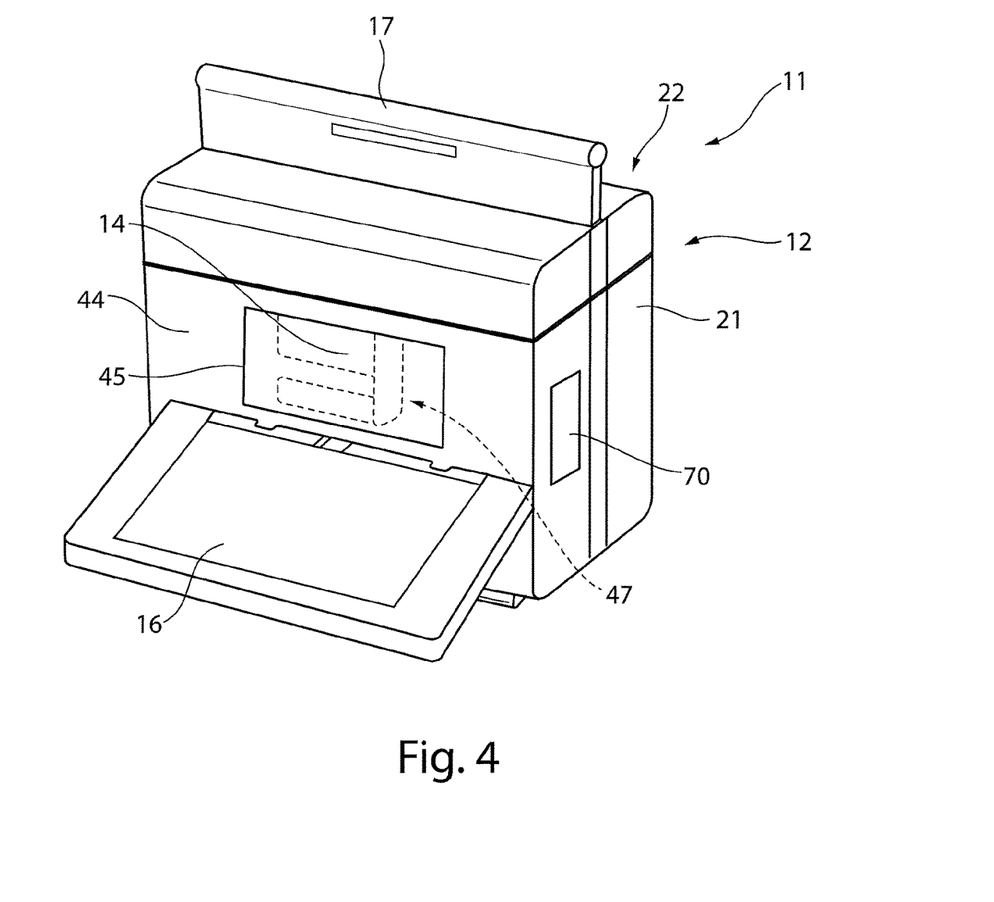

In FIGS. 3 and 4, the mobile device 11 for the x-ray fluorescence analysis is depicted in a first application as a desktop instrument.

The display 16 or a data processing device having the display 16, such as, for example, a removable tablet, is provided on a front side of the transport container 12, said display 16 being able to be folded out from a non-use position according to FIG. 1 into a use position depicted in FIGS. 3 and 4. For example, the display 16 is able to be pivoted out around a horizontal rotational axis, as is depicted in FIGS. 3 and 4. The rotational axis can also be provided at an upper or lower end. Likewise, a vertical rotational axis can also be provided in a corner region of the side surface of the transport container. A receiving space for the display 16 or the data processing device on the transport container 12 is separated by a partition 44 with respect to the inner space of the transport container 12. This partition 44 can have a window 45 which is formed to be transparent in order to be able to check optically that the handheld instrument 14 is arranged in a stowage position 47 in the lower part 21 of the transport container 12.

For the implementation of a measurement on a measurement object 39, the cover 22 is opened such that the measurement object 39 can be supported on a measurement table 48 which is part of a receiver 49. This receiver 49 has a flat plane and is preferably formed as a plate which is supported on an upper edge 51 of the lower part 21 and preferably is able to be removed completely or at least partially. A through-hole 52 is provided in the receiver 49. The handheld instrument 14 is fastened to a mount 54 depicted in FIGS. 5 to 8 with respect to the through-hole on a side of the receiver 49 which opposes the measurement table 48 such that an outlet window 31 of the handheld instrument 14 is allocated directly to the through-hole 52. During the positioning of the receiver 49 in a use position 42 and of the handheld instrument 14 in the stowage position 47, the handheld instrument 14 is provided in the inner space of the lower part 21 and is completely surrounded by the lower part 21 and the receiver 49. A measurement on a measurement surface 38 of the measurement object 39 can thereby occur which is supported facing forwards with the measurement surface 38 on the measurement table 48. A measurement object 39 supported on the measurement table 48 is positioned in such a way that a measurement surface 38 lies in the region of the through-hole 52 or covers this.

An absorption element 56 is provided on an inner side of the cover 12, said absorption element 56 lying in a radiation axis of an x-ray radiation in the case of a closed cover 22, said x-ray radiation exiting through the though-hole 52 in order to absorb the x-ray radiation which potentially exits through the through-hole 52.

The handheld instrument 14 and the data processing device work preferably wirelessly such that the signals detected by the x-ray measurement device are evaluated by means of the evaluation unit thereof and are transmitted to the data processing device for preparation and emission of the detected values. The cover 22 is closed for the implementation of a measurement after the support of the measurement object 39 on the receiver 49 and alignment with respect to the through-hole 52. A signal is thereby transferred to the x-ray fluorescence device such that a measurement can be released and started. The handheld instrument 14 arranged in the lower part 21 communicates either wirelessly with the data processing device or a cable connection is provided between the handheld instrument 14 and the data processing device, as this is depicted, for example, schematically in FIG. 5 by the data transfer cable 46. Individual parameters or standards for the implementation of the measurement can be entered via the display 16 and the measurement can be started by the user. After the implementation of the measurement, the measurement result is emitted in corresponding diagrams. As soon as the cover 22 is lifted for the removal of the measurement object 39, a blocking of the x-ray fluorescence measurement device in the handheld instrument 14 occurs automatically such that a primary radiation cannot be emitted accidently from the handheld instrument 14.

Figure 5:
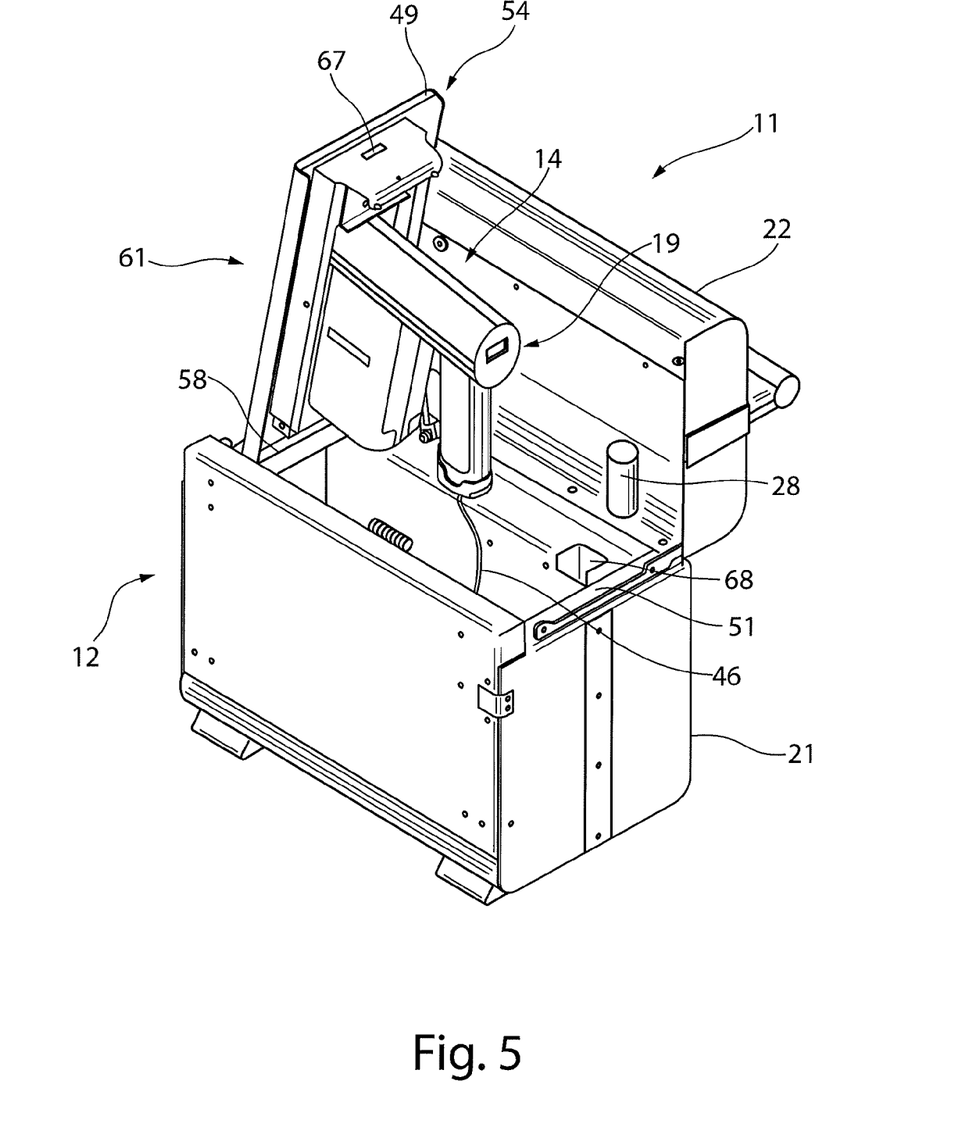
Figure 6:
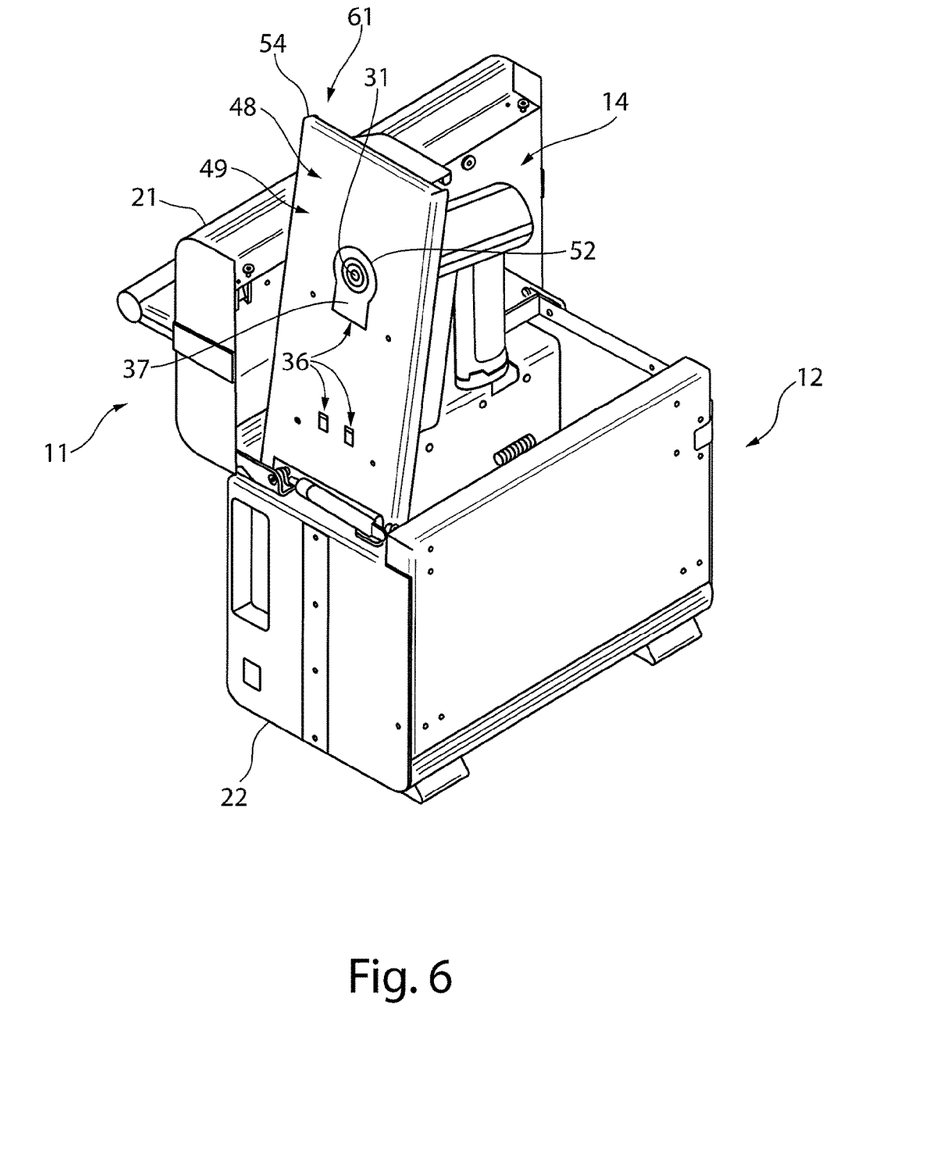
Figure 7:
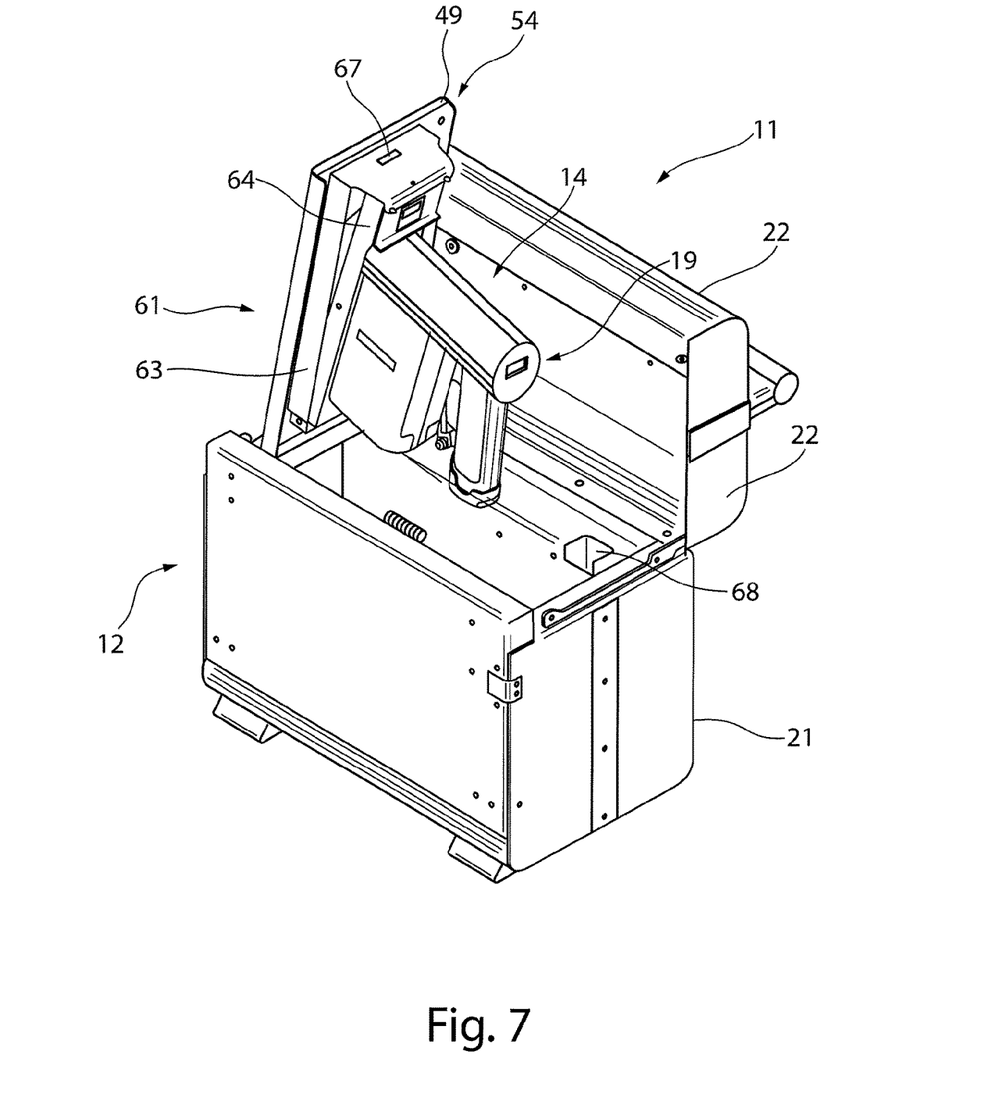
Figure 8:
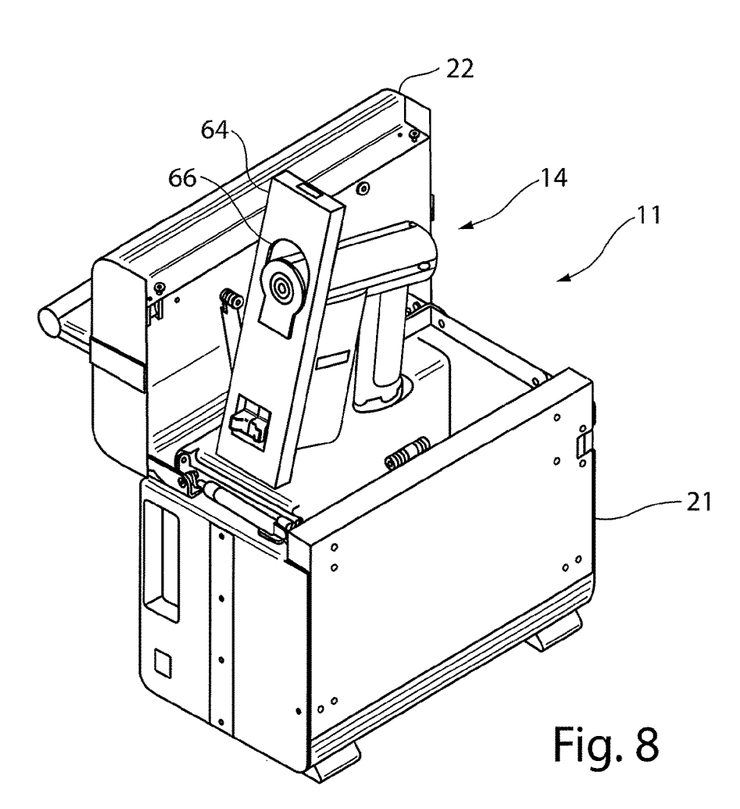
Figure 9A:
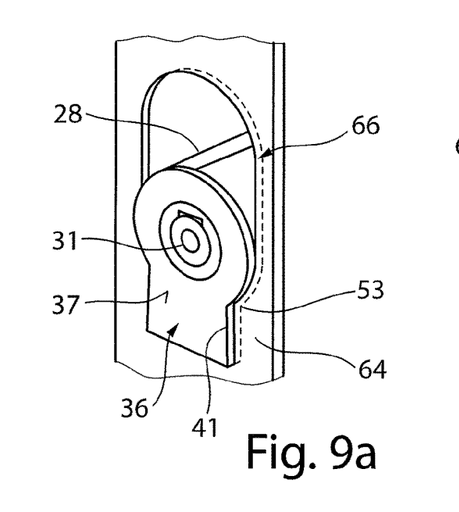
Figure 9B:
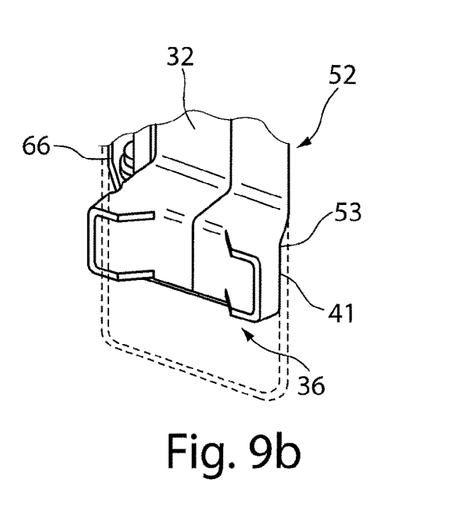

In FIGS. 3, 5 to 9, a sequence of work steps is depicted in order to transfer the handheld instrument 14 from its stowage position 47 into a use positioning 57 in which the mobile handheld instrument 14 is positioned directly on the measurement object 39 according to FIG. 11 and is positioned with respect to the measurement object 39. FIG. 6 shows an analogous arrangement to FIG. 8, wherein in FIG. 8, the receiver 49 is not depicted. The receiver 49 is preferably connected to the transport container 12, preferably the lower part 21, via a hinge joint 58 on a longitudinal or narrow side, such that the receiver 49 can be transferred from a stowage position 47 according to FIG. 3 into a removal position 61 according to FIG. 7 for the handheld instrument 14 by a pivot movement. The mount 54 for the receiver 49 of the handheld instrument 14 and for fixing to the through-hole 52 is evident in this removal position 61. The mount 54 for the handheld instrument 14 is only exemplary and can be solved in different ways by releasable plug, clamp, catch and/or bayonet connections.

This mount 54 encompasses, for example, a base plate 63 which is arranged fixedly on the lower side of the receiver 49, as well as a carrier plate 64 which is arranged to be able to pivot with respect to the base plate 63 in order to position and to fix the handheld instrument 14 which is arranged on the carrier plate 64 with respect to the base plate 63 by a clamping. For this purpose, the carrier plate 64 has openings 66 which are preferably formed to be keyhole-shaped, as emerges from FIGS. 9a and 9b. It is thereby enabled that the support elements 36 of the handheld instrument 14 having the fastening elements 41 arranged laterally thereon are able to be inserted into the wider section of the opening 66 such that these fastening elements 41 engage with the narrower sections of the opening 66 and/or engage behind these. Preferably, the narrower section of the opening 66 can also be formed to be conical such that an additional centring of the handheld instrument 14 with respect to the openings 66 of the carrier plate 64 is enabled. After the handheld instrument 14 having the fastening elements 41 is inserted into the openings 66 of the carrier plate 64 and has assumed a lower position, the carrier plate 64 is pivoted closed on the base plate 63 and is fastened by means of a fixing element 67, such as, for example a clamping, latching or screwing. Such a position is depicted in FIG. 5. The handheld instrument 14, in particular the longitudinal axis of the first housing section 30, is therefore aligned exactly with respect to the passage opening 52. Preferably, the support surface 37 of the handheld instrument 14 is flush to the surface of the measurement table 48 such that a closed support surface is formed on the receiver 49 in order to position a measurement object 39 to be supported thereon, as this is, for example, depicted in FIG. 3. Alternatively, the outlet window 31 or the support surface 37 can be offset backwards compared to the support surface of the measurement table 48.

A removal of the handheld instrument 14 occurs in reverse order to the previously described assembly of the handheld instrument 14 on the mount 54. After the transfer of the receiver 49 into the removal position 61, the fixing 67, for example a screwing or clamping, can be resolved. The carrier plate 64 is thereby removed from the base plate 63 by a pivot movement (FIG. 7) such that the handheld instrument 14 having the support elements 36 is firstly driven upwards within the opening 66 until the fastening elements 41 have reached the wider region of the openings 66 in order to subsequently remove the handheld instrument 14 from the openings 66.

The transport container 12 can furthermore have at least one stowage space 68 for a further accumulator 28. Advantageously, the transport container 12 itself comprises its own energy supply in the form of a rechargeable accumulator 28, using which the electric instruments arranged and/or connected in the transport container 12 can be charged. Additionally, a connection line for a connection 70 (FIG. 4) to a public power supply can be provided on the transport container 12 in order to enable an energy supply and/or a recharging of the accumulators 28.

Figure 10:
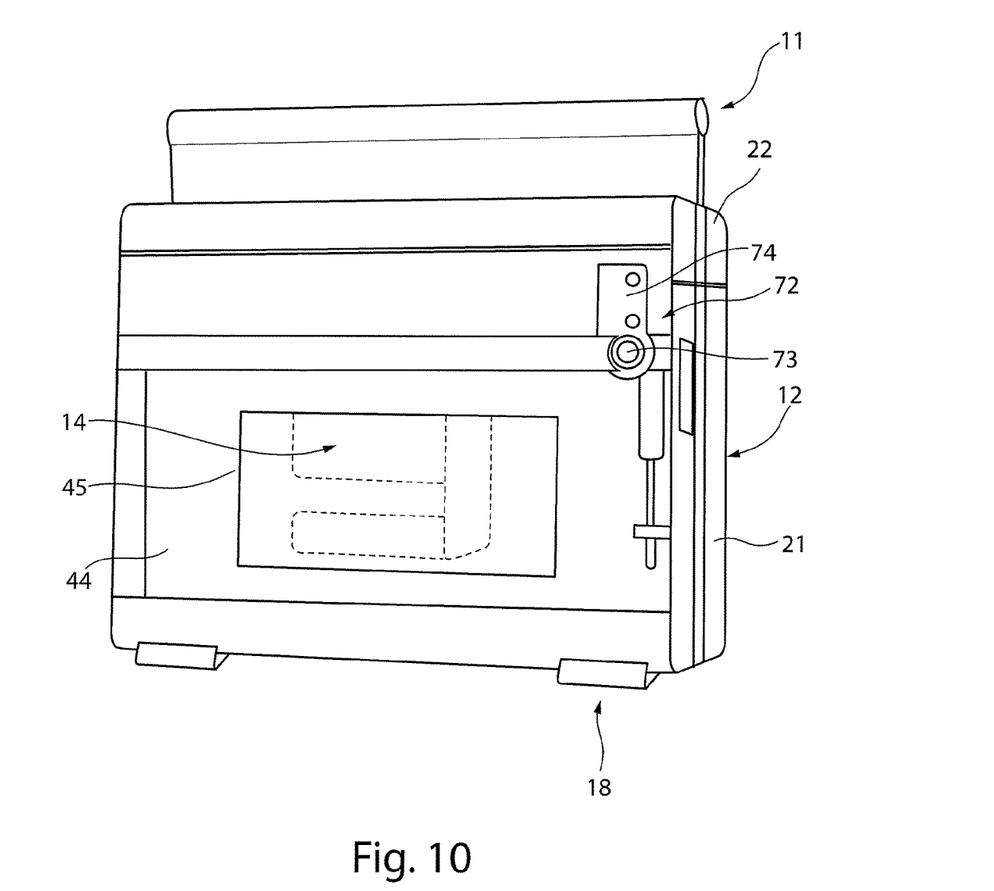

In FIG. 10, a schematic partial view onto a transport container 12 is depicted in which the display 16 or the data processing device is completely removed. A locking mechanism 72 is thereby visible which preferably comprises a central lock over the lock 73. A slide bar 74 of the locking mechanism 72 enables, on the one hand, a securing of the cover 22 with respect to the lower part 21 as well as a transport position of the display 16 or the data processing device with respect to the transport container 12. An accessibility in the inner space of the transport container 12 is no longer possible from the outside.

The invention claimed is:

1. A handheld instrument for x-ray fluorescence analysis comprising:
   a housing;
   an x-ray fluorescence measurement device arranged in the housing, the measurement device comprising a radiation source, by which a primary beam is directed onto a measurement surface of a measurement object through an outlet window,
   a detector arranged in the housing which detects the secondary radiation emitted by the measurement surface of the measurement object, and
   a data processing device arranged in the housing, which controls at least one display which is provided on the housing or is connected to the housing, wherein
   the outlet window is provided on a front-side end of a first housing section of the housing and at least one positioning element is provided on the first housing section, allocated to this outlet window,
   at least one support element is provided on at least one further housing section of the housing, and
   the handheld instrument being configured for alignment with respect to the measurement surface after the positioning of the at least one support element of the handheld instrument on the measurement surface of the measurement object, and the handheld instrument being configured to be self-supporting on the measurement surface by the at least one positioning element and the at least one support element, the handheld instrument being positionable autonomously with respect to the measurement surface in a measurement position by way of the at least one positioning element and the at least one support element,
   wherein the at least one support element includes two support elements, the at least one positioning element and the two support elements forming a three-point support, or wherein the at least one positioning element includes two positioning elements, the two positioning elements and the at least one support element forming a three-point support.

2. The handheld instrument according to claim 1, wherein the housing includes a handle provided on the first housing section.

3. The handheld instrument according to claim 1, wherein the at least one positioning element which is adjacent to the outlet window or abuts onto the outlet window is formed as a support surface and the at least one support element arranged on the housing section is formed as a positioning foot.

4. The handheld instrument according to claim 1, wherein fastening elements for fixing the handheld instrument to a receiver or a mount are provided on the receiver of a measurement table, adjacent to the at least one support element or on the at least one support element.

5. The handheld instrument according to claim 1, wherein the data processing device controls a radio interface for wireless communication with a further data processing device which is provided separately to the handheld instrument.

6. The handheld instrument according to claim 1, wherein the data processing device in the handheld instrument is able to be controlled by means of a remote control.

7. A mobile device for x-ray fluorescence analysis, comprising:
   a portable transport container the handheld instrument according to claim 1,
   the x-ray fluorescence measurement device provided in the handheld instrument according to claim 1, the handheld instrument being able to be arranged in the transport container and is able to be removed completely from the transport container,
   a receiver which is able to be arranged in the transport container, which at least partially forms a measurement table on which a measurement object is able to be arranged, wherein the handheld instrument is able to be positioned in the transport container with respect to the measurement table, wherein the handheld instrument is able to be fastened releasably on the receiver and is able to be arranged in the transport container, and
   the receiver is formed on one side as a measurement table and a mount for the releasable fastening of the handheld instrument is provided on an opposite side of the receiver.

8. The handheld instrument according to claim 1, wherein the at least one support element includes at least one laterally extending surface for engaging the measurement surface.

9. The handheld instrument according to claim 2, wherein the at least one further housing section is connected to the first housing section and the first housing section and the handle are formed to be pistol-shaped.

10. The device according to claim 7, wherein a through-hole is provided in the receiver and the handheld instrument is able to be positioned with respect to or in the through-hole of the receiver using the mount and the handheld instrument is fastened to the mount of the receiver using a plug, clamp or screw connection or a bayonet lock.

11. The device according to claim 7, wherein the transport container has a lower part and a cover which is able to close the lower part and which is arranged on the lower part to be able to be folded open or to be removable and in a closed position with respect to the lower part, the cover fixes the receiver to the lower part of the transport container.

12. The device according to claim 7, wherein the receiver having a hinge connection is arranged on a side wall of the transport container and the receiver is able to be transferred from a stowage position into a removal position to remove the handheld instrument.

13. The device according to claim 7, wherein the mount has at least one centering and/or fixing section for the correct positioning of the handheld instrument with respect to the through-hole of the receiver.

14. The device according to claim 7, wherein the mount has at least one opening into which the fastening elements of the handheld instrument are able to be inserted and are able to be arranged in a fastening position with respect to the mount.

15. The device according to claim 7, wherein the support mount is flush with an upper surface of the measurement table.

16. The device according to claim 11, wherein an absorption element is provided in the cover of the transport container, which is situated above the through-hole in a stowage position of the receiver.

17. The device according to claim 11, wherein the lower part of the transport container has a pivotable and/or removable display and/or the data processing device having the display on an outer side, which is able to be transferred from a non-use position for transport of the transport container into a use position for the use of the device for x-ray fluorescence analysis.

18. The device according to claim 17, wherein a wireless communication between the handheld instrument and the data processing device or the display or both of the transport container, is provided.

\* \* \* \* \*

UNITED STATES PATENT AND TRADEMARK OFFICE
CERTIFICATE OF CORRECTION

Page 1 of 1

PATENT NO. : 10,078,060 B2
APPLICATION NO. : 14/805926
DATED : September 18, 2018
INVENTOR(S) : Udo Geier and Bernhard Nensel It is certified that error appears in the above-identified patent and that said Letters Patent is hereby corrected as shown below:

In the Claims

In Claim 7 at Lines 66-67, the word --for-- should be inserted between "a portable transport container" and "the handheld instrument according to claim 1,".

Signed and Sealed this
Fifth Day of March, 2019

Andrei Iancu
*Director of the United States Patent and Trademark Office*